(12) United States Patent
Hadipour-Niktarash

(10) Patent No.: US 12,201,842 B2
(45) Date of Patent: Jan. 21, 2025

(54) STEREOTACTIC MULTIFOCAL RECORDING AND STIMULATION DEVICE AND METHODS OF USE

(71) Applicant: STEREONEUROSTIM, LLC, Denver, CO (US)

(72) Inventor: Arash Hadipour-Niktarash, Denver, CO (US)

(73) Assignee: United States Government As Represented By The Department Of Veterans Affairs, Washington, DC (US)

( * ) Notice: Subject to any disclaimer, the term of this patent is extended or adjusted under 35 U.S.C. 154(b) by 385 days.

(21) Appl. No.: 17/848,744

(22) Filed: Jun. 24, 2022

(65) Prior Publication Data

US 2023/0009281 A1    Jan. 12, 2023

Related U.S. Application Data

(63) Continuation of application No. 16/730,544, filed on Dec. 30, 2019, now Pat. No. 11,369,797.

(60) Provisional application No. 62/791,367, filed on Jan. 11, 2019.

(51) Int. Cl.
```
A61N 1/375      (2006.01)
A61B 5/293      (2021.01)
A61N 1/05       (2006.01)
A61N 1/36       (2006.01)
```

(52) U.S. Cl.
CPC .......... *A61N 1/36185* (2013.01); *A61B 5/293* (2021.01); *A61N 1/3756* (2013.01); *A61N 1/36064* (2013.01); *A61N 1/36067* (2013.01); *A61N 1/36082* (2013.01)

(58) Field of Classification Search
USPC .................................. 607/148, 128
See application file for complete search history.

(56) References Cited

U.S. PATENT DOCUMENTS

| | | | | |
|---|---|---|---|---|
| 5,507,802 A | * | 4/1996 | Imran | A61N 1/05 607/128 |
| 2002/0151888 A1 | * | 10/2002 | Edwards | A61B 18/1485 606/41 |
| 2021/0128229 A1 | * | 5/2021 | Panescu | A61B 5/4041 |

* cited by examiner

*Primary Examiner* — Kennedy Schaetzle
(74) *Attorney, Agent, or Firm* — Ballard Spahr LLP

(57) ABSTRACT

A neural stimulation and recording electrode assembly includes a selectively deformable guide tube. The guide tube includes a plurality of sequentially coupled connecting structures, wherein each connecting structure of the plurality of connecting structures has a respective central axis, and wherein at least one of the plurality of connecting structures is selectively deformable relative to the central axis of a sequential connecting structure of the plurality of connecting structures such that the central axis of the selectively deformable connecting structure is angularly oriented relative to the central axis of the sequential connecting structure. The electrode assembly further includes an electrode subassembly having a central axis and a plurality of electrode contacts that are configured for selective radial movement about and between a retracted position and a deployed position, wherein in the deployed position, and relative to the central axis, each electrode contact is spaced radially outwardly from the retracted position.

20 Claims, 14 Drawing Sheets

STEREOTACTIC MULTIFOCAL RECORDING AND STIMULATION DEVICE AND METHODS OF USE

CROSS-REFERENCE TO RELATED APPLICATIONS

This application is a continuation of U.S. patent application Ser. No. 16/730,544, filed Dec. 30, 2019, which claims priority to and the benefit of U.S. Provisional Patent Application No. 62/791,367, filed Jan. 11, 2019. The entirety of which each of which hereby incorporated by reference herein.

FIELD

This disclosure relates to systems having neural stimulation electrodes and recording electrodes and methods of using such systems.

BACKGROUND

In various neurological disorders, the underlying pathology is an abnormal complex neuronal network which involves spatially distributed brain regions within cortical grey, deep white and grey matter, or grey-white matter interface. These disorders include but are not limited to multilesional epilepsy, including tuberous sclerosis (TS), focal cortical dysplasia (FCD), periventricular nodular heterotropia, postinfection encephalitis, posttraumatic epilepsy, vascular injuries, tumors (in particular, brain metastases), postradiation epilepsy, etc. These disorders also include various type of non-epilepsy disorders including but not limited to tumors, Central Nervous System (CNS) pain syndromes, psychiatric disorders, multiple sclerosis, and various movement disorders including Parkinson's disease, dystonia, and tremor.

Epilepsy is a common and devastating neurological disorder, affecting more than 70 million people worldwide. Initially, antiepileptic drugs (AEDs) are used to control seizure. However, about 30% of patients do not respond to AEDs and develop refractory epilepsy when seizures cannot be controlled by at least two or three AEDs chosen appropriately for the epilepsy type. The effectiveness of epilepsy surgery in the management of medically refractory focal epilepsy is currently widely accepted. Evaluation for epilepsy surgery should be entertained early in the course of the disease. With appropriate consideration of risks and benefits and in carefully selected patients, there is extensive evidence about highly favorable risk-benefit ratio of epilepsy surgery, neurostimulation and neuromodulation procedures, as well as of its positive impact on psychological aspects and quality of life. Patients who are considered for epilepsy surgery undergo extensive evaluation to determine that any specific surgical procedure will be effective in controlling seizures without unacceptable risks.

There are several steps involved in the presurgical evaluation of patients prior to consideration for epilepsy surgery, neuromodulation and neurostimulation procedures, One of the presurgical steps includes stereo-electroencephalography (SEEG) method. Using SEEG method, depth electrodes are inserted using multiple orthogonal or oblique orientations, allowing recording from deep cortical and subcortical epileptic and normal structures in a 3-dimensional arrangement, thus conceptualizing the dynamic, multidirectional spatiotemporal organization of the epileptic pathways.

Patients with medically refractory epilepsy who are not a good candidate for focal and multilesional resection, might benefit from other type of surgical procedures including, grey and white matter electrical stimulation, neuromodulation procedures, corpus callosotomy, and functional disconnective procedures.

In order to perform stimulation and recording from multiple foci in 3-dimensional arrangement using conventional straight electrodes and conventional implantation methods, it is necessary to implant multiple electrodes through several trajectories with different orientations, which might result in a significant tissue damage along the trajectories. In addition, and more importantly, using conventional approaches and conventional recording and stimulation electrodes, contacts are not always placed precisely within the desired proximity of targets, and, therefore, recorded epileptic discharge and delivered stimulation might not be optimal.

Using conventional depth electrode and SEEG intracranial placement and recording methods used in current clinical practice, after electrodes are implanted, spatial locations of the electrode(s) contacts remain locked and immobile throughout the recording phase.

Once the electrodes are positioned near a target, the electrodes can be deployed via an electrode subassembly from a first position to a second position with respect to a delivery structure. An example of such an electrode subassembly can be shown in U.S. Pat. No. 9,750,422 to Zino et al., which is incorporated by reference herein for all purposes. However, conventional electrode subassemblies cannot be retracted and redeployed. Therefore, if the electrode subassembly is improperly placed, it cannot be repositioned and must be completely removed.

SUMMARY

Disclosed herein, in one aspect, is a stereotactical multifocal recording and stimulation device and methods of use therefor.

The stereotactical multifocal recording and stimulation device provides a mechanism to rearrange the 3-dimensional spatial position of the electrode contact(s) during the recording phase. The aforementioned spatial rearrangeable feature of the present disclosure provides more precise electric charge recording and more relevant sets of recording data (which is used for planning chronic neurostimulation/neuromodulation device/electrode implantation) by dynamic rearrangement of spatial positions of the electrode contacts based on the growing recorded brain activity data and hypotheses that are regularly and dynamically build during the recoding phase. Using the stereotactical multifocal recording and stimulation device and disclosed placement methods, electrode contacts can be implanted more precisely within the desired proximity of targets and epileptic foci using minimum number of steerable deformable guild tube(s) and electrode(s) assembly through 3-dimensional spatial curved trajectories, and therefore there will be less damage to the brain tissue. More importantly, the present novel assembly provides more precise epileptic discharge recording and more precise and efficient electric charge delivery and stimulation to targets/epileptic foci.

Some of the beneficial effects of the spatially rearrangeable aspect of the present recording/stimulation device can also apply to chronic recording and stimulation devices/electrode procedures. This aspect provides a mechanism to deliver electric charge and stimulation more efficiently by dynamic rearrangement of spatial locations of electrode contacts based on the continuing recorded brain activity data set and new hypothesis that are dynamically built during the chronic recording and stimulation phase.

The rational for favorable effects of the spatial rearrangeable aspect of the present recording/stimulation assembly also applies to non-epilepsy neurological disorders with underlying multifocal pathology as well (e.g. Parkinson's disease: multi-target deep brain stimulation strategy), and avoiding stimulation of regions which cause undesirable side effects, like internal capsule stimulation during DBS therapy for Parkinson's disease).

In neurological conditions with chronically implanted stimulation device/electrode (e.g. epilepsy, movement disorders, pain disorders, etc.), the present novel guide tube and recording/stimulation assembly with its dynamic spatial rearrangeable aspect provides the mechanism to avoid stimulation of regions which might cause undesirable side effects (e.g. Parkinson's disease: avoiding sensory-motor side effect by internal capsule stimulation in movement disorders DBS stimulation). Furthermore, in order to have more efficient neurostimulation, spatial locations of the electrode contacts can be rearranged anytime during the chronic implantation period. This rearrangement can be guided by patient's clinical response, side effects, growing recorder brain activity data, and new hypotheses that are continuously and dynamically built during chronic implantation phase as the patients' disease evolves.

Electrical stimulation of many central nervous system (CNS) structures, in various forms, has been proposed for the treatment of epilepsy and non-epilepsy neurological disorders. These brain structures include fornix, thalamus, caudate, subthalamic nucleus, hippocampus, cortex, corpus callosum, hypothalamus, locus coeruleus, and cerebellum. Although the idea of directly stimulating the cortex is appealing, for various reasons, white matter stimulation might be a good alternative for treatment of epilepsy. In several neurological conditions (e.g. large cortical dysplasia), the epileptogenic or pathologic tissue is significantly larger than the spatial effective distribution of the electric field of the stimulation electrode(s). Thus, neuromodulation of large cortical epileptogenic/pathologic tissue, using limited numbers of conventional stimulation electrode, can be suboptimal. With the goal of delivering efficient electric current to large epileptogenic tissue, stimulation of small cross-sectional diameter of compact white matter axons can allow the electric field current to propagate to the large cortical epileptogenic tissue and modulate its function more efficiency in comparison to direct stimulation of epileptogenic tissue, using limited numbers of conventional cortical strip leads.

In order to stimulate a specific part of white matter tracts in a 3-dimensional arrangement, using conventional electrodes and conventional implantation methods currently used in clinical practice, it is necessary to implant multiple electrodes through multiple trajectories with different orientations, which might result in a significant tissue damage along the trajectories. In addition, and more importantly, using conventional approaches and conventional stimulation electrodes, due to suboptimal 3-dimensional spatial arrangement of stimulation electrode contacts with respect to the target white matter tracts, spatial electric field of the stimulation electrode might not precisely and effectively modulate the target white matter tracts.

Using neuroimaging (e.g. diffusion tensor imaging) and computational techniques, optimal spatial 3-dimentional arrangement of the stimulation electrode contacts with respect to the target white matter trajectory (associated with seizure focus and transmission pathways) can be precisely determined to deliver optimal electric field to the target fibers tracts. In contrast with conventional electrodes currently used in clinical practice, using the disclosed, guide tube and stimulation/recording electrode device, electrode(s) can be flexibly implanted in a 3-dimensional curved trajectory to mimics the optimal predetermined electrode trajectory which provides optimal 3-D stimulation therapy. In addition, in order to perform more efficient neurostimulation, spatial location of the electrode contacts can be rearranged anytime during the chronic implantation period. This rearrangement can be based on patient's clinical response, side effects, growing recorder brain activity data, and new hypotheses that are continuously and dynamically built during the chronic implantation phase as the patients' disease evolves.

A neural stimulation and recording electrode assembly can comprise a selectively deformable guide tube having a length. The guide tube can include a plurality of sequentially coupled connecting structures. Each connecting structure of the plurality of connecting structures can have a respective central axis. At least one of the plurality of connecting structures can be selectively deformable relative to the central axis of a sequential connecting structure of the plurality of connecting structures such that the central axis of the selectively deformable connecting structure is angularly oriented relative to the central axis of the sequential connecting structure. The neural stimulation and recording electrode assembly can further comprise an electrode subassembly having a central axis and a plurality of electrode contacts that are configured for selective radial movement about and between a retracted position and a deployed position. In the deployed position, and relative to the central axis, each electrode contact is spaced radially outwardly from the retracted position.

Each of the at least one selectively deformable connecting structure of the guide tube can be configured to be selectively independently deformed as the selectively deformable connecting structure is advanced within a tissue region.

Each of the plurality of connecting structures can be selectively deformable relative to the central axis of a sequential connecting structure of the plurality of connecting structures such that the central axis of the selectively deformable connecting structure is angularly oriented relative to the central axis of the sequential connecting structure.

Each of the at least one selectively deformable connecting structure can be selectively compressible and expandable relative to the central axis of the connecting structure. The selectively deformable guide tube can be deformable from a first compressed orientation to a second expanded orientation. In the second expanded orientation, at least one of the selectively deformable connecting structures can be axially expanded in comparison to the first compressed orientation.

Each of the plurality of connecting structures can comprise springs.

Each of the connecting structures can further comprise rings attached at each end of the spring of the respective connecting structure.

The plurality of joints and the plurality of connecting structures can have respective lengths. The length of each connecting structure of the plurality of connecting structures can be greater than the length of each joint of the plurality of joints.

The length of at least one connecting structure of the plurality of connecting structures can be different than the length of at least one other connecting structure of the plurality of connecting structures.

The electrode subassembly can comprise a plurality of branches extending radially outwardly from the central axis of the electrode subassembly. The plurality of electrode contacts can be provided on respective branches of the plurality of branches. Each branch can be selectively radially moveable to effect movement of a corresponding electrode contact about and between the retracted position and the deployed position.

Each branch can be selectively angularly deformable relative to the central axis of the shaft to effect movement of a corresponding electrode contact about and between the retracted position and the deployed position.

The electrode subassembly can further comprise an annular body having an outer surface and an inner surface that defines an axial bore. The plurality of electrode contacts can be coupled to the outer surface of the annular body. A selectively inflatable balloon can be positioned within the axial bore of the annular body. The annular body can comprise a flexible material that permits radial expansion and compression of the annular body in response to selective inflation and deflation of the balloon.

The electrode subassembly can further comprise an annular body defining an axial bore and a plurality of sets of circumferentially spaced openings. The plurality of sets can be axially spaced along a length of the annular body. A selectively inflatable balloon can be positioned within the axial bore of the annular body. The selectively inflatable balloon can have an outer surface to which the plurality of electrode contacts can be coupled. In response to selective inflation and deflation of the balloon, the plurality of electrode contacts can be configured for radial expansion and retraction through corresponding openings of the annular body.

The electrode subassembly can further comprise an annular body defining an axial bore and a plurality of openings that are axially spaced along a length of the annular body. A selectively inflatable balloon can be positioned within the axial bore of the annular body. The selectively inflatable balloon can have an outer surface to which the plurality of electrode contacts are coupled. In response to selective inflation and deflation of the balloon, the plurality of electrode contacts can be configured for radial expansion and retraction through corresponding openings of the annular body.

The electrode subassembly can further comprise an annular body defining an axial bore and a plurality of openings and a selectively inflatable balloon positioned within the axial bore of the annular body. The selectively inflatable balloon can have an outer surface and a plurality of rods extending radially outwardly from and being coupled to the outer surface of the balloon. A respective electrode contact can be secured to a distal end of each rod. In response to selective inflation and deflation of the balloon, the plurality of rods can be configured for corresponding radial movement.

The plurality of rods can be circumferentially spaced about the outer surface of the balloon.

The plurality of rods can be axially spaced along an axial length of the balloon.

A method of using the neural stimulation and recording electrode array can comprise: selectively and sequentially deforming at least one connecting structure of the guide tube to define an insertion pathway; and advancing the electrode subassembly through the guide tube until at least a portion of the plurality of electrode contacts are positioned at a selected position within selected a tissue region; effecting movement of at least a first portion of the plurality of electrode contacts from the retracted position to the deployed position.

The method can further comprise: retracting the at least a first portion of the plurality of electrode contacts from the deployed position to the retracted position; adjusting the position of the electrode subassembly within the tissue region; and effecting movement of a second portion of the plurality of electrode contacts from the retracted position to the deployed position.

The at least one electrode contact of the second portion of the plurality of electrode contacts can be exclusive of the first portion of the plurality of electrode contacts.

The method can further comprise electrically stimulating tissue within the tissue region using the plurality of electrode contacts.

The electrode subassembly can comprise: an annular body defining an axial bore and a plurality of openings; a selectively inflatable balloon positioned within the axial bore of the annular body, wherein the selectively inflatable balloon has an outer surface; and a plurality of rods extending radially outwardly from and being coupled to the outer surface of the balloon, wherein a respective electrode contact is secured to a distal end of each rod, wherein, in response to selective inflation of the balloon, the plurality of rods undergo corresponding radial movement to enter into target tissue.

The target tissue can comprise brain parenchyma. The plurality of rods and corresponding electrode contacts can enter target tissue through a ventricle wall.

A guide tube can have a length and comprise: plurality of sequentially coupled connecting structures. Each connecting structure of the plurality of connecting structures can have a respective central axis. At least one of the plurality of connecting structures can be selectively deformable relative to the central axis of a sequential connecting structure of the plurality of connecting structures such that the central axis of the selectively deformable connecting structure is angularly oriented relative to the central axis of the sequential connecting structure.

Additional advantages of the disclosed system and method will be set forth in part in the description which follows, and in part will be understood from the description, or may be learned by practice of the disclosed system and method. The advantages of the disclosed system and method will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed apparatus, system, and method and together with the description, serve to explain the principles of the disclosed apparatus, system, and method.

DETAILED DESCRIPTION

Figure 1:
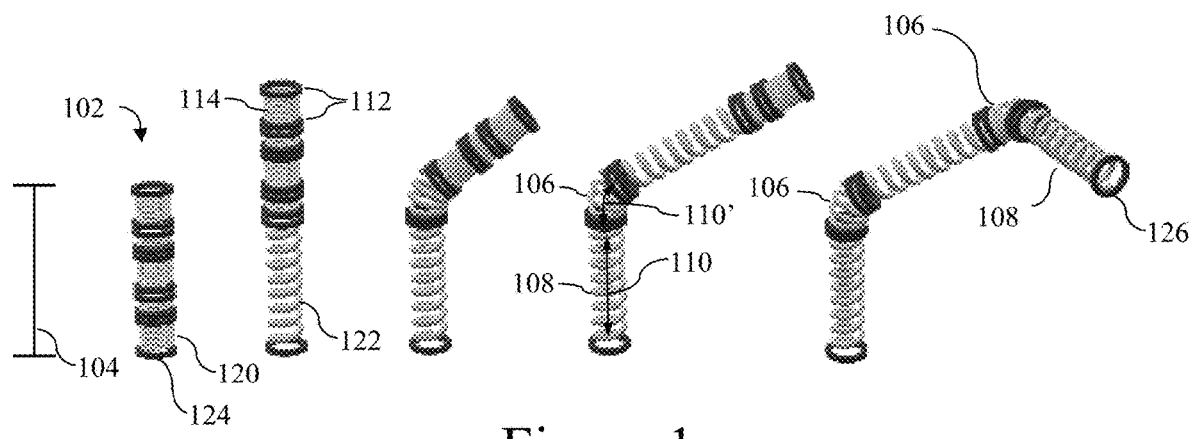
FIG. 1 illustrates a plurality of perspective views of a guide tube for use in a neural stimulation device according to disclosed embodiments in various stages of progression, with sequentially alternating expansion of support structures and deformations of joints.

The disclosed system and method may be understood more readily by reference to the following detailed description of particular embodiments and the examples included therein and to the Figures and their previous and following description.

A. Definitions

It is to be understood that, the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural references unless the context clearly dictates otherwise. Thus, for example, reference to "an elbow" includes a plurality of such elbows, and reference to "the elbow" is a reference to one or more joints and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed apparatus, system, and method belong. Although any apparatus, systems, and methods and materials similar or equivalent to those described herein can be used in the practice or testing of the present apparatus, system, and method, the particularly useful methods, devices, systems, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications may be referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Neural Stimulation and Recording Electrode Assembly

Figure 2:
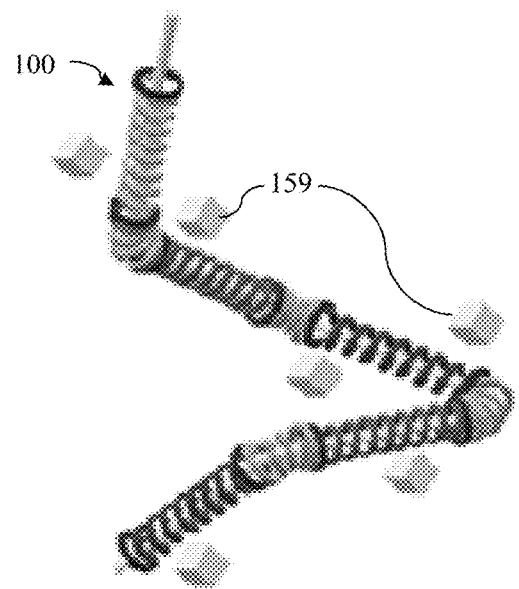
FIG. 2 is a perspective view of the guide tube as in FIG. 1 proximate multifocal targets.
Figure 3:
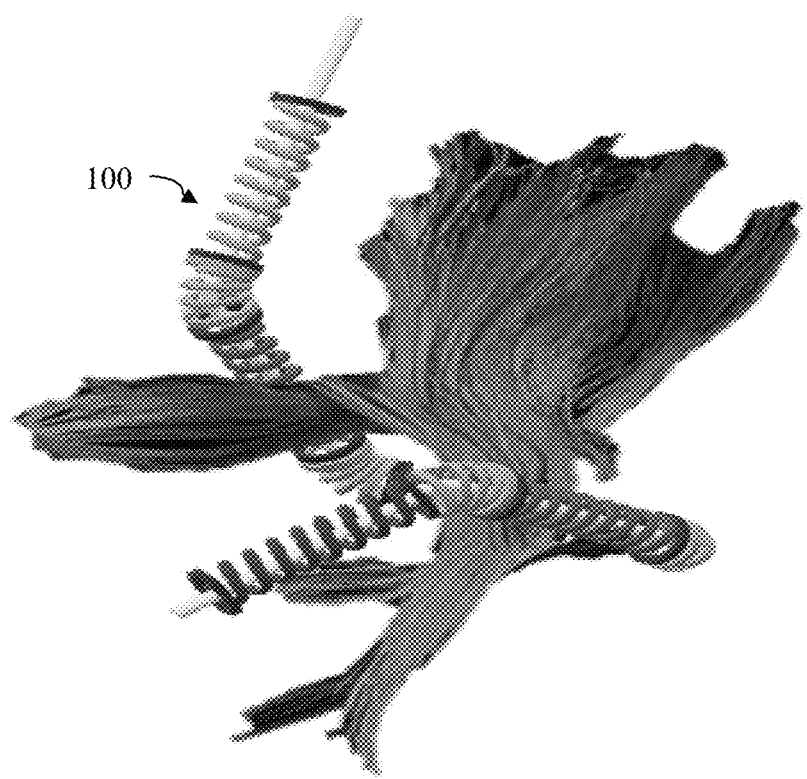
FIG. 3 illustrates the guide tube as in FIG. 2 with representative brain white matter tract according to disclosed embodiments.

Disclosed herein is a neural stimulation recording electrode assembly. Referring to FIGS. 1-3, a neural stimulation recording electrode assembly 100 (shown in part) can include a guide tube 102 having a length 104. The guide tube 102 can comprise a plurality of elbows 106 spaced apart relative to the guide tube's length. A plurality of linearly elongatable structures 108 can be positioned between and coupled to sequential elbows 106. The elbows and linearly elongatable structures can collectively be referred to as "connecting structures." Each connecting structure can have its own respective central axis 110. The central axis 110 of a given connecting structure can be defined as a line that extends through a center of the connecting structure along its length. Each elbow 106 can be deformable so that its central axis 110' can be angularly oriented with respect to a central axis 110 of an adjacent connecting structure. It should be understood that a central axis of a first connecting structure is angularly oriented with respect to a central axis of a second connecting structure if at least a portion of the first connecting structure's central axis 110 is angularly oriented with respect to at least a portion of the second connecting structure's central axis 110'. Each of the elbows 106 and the linearly elongatable structures 108 can comprise a pair of spaced rings 112 that are connected by a spring 114. Moreover, each linearly elongatable structure can be selectively deformable from a first, compressed state 120 to a second, elongated state 122 that is axially expanded in comparison to the first, compressed state. In some embodiments, the elongated state 122 can be selected on a continuum between the compressed state 120 and a completely uncompressed state in which the connecting structure is at its maximum elongation.

Figure 4:
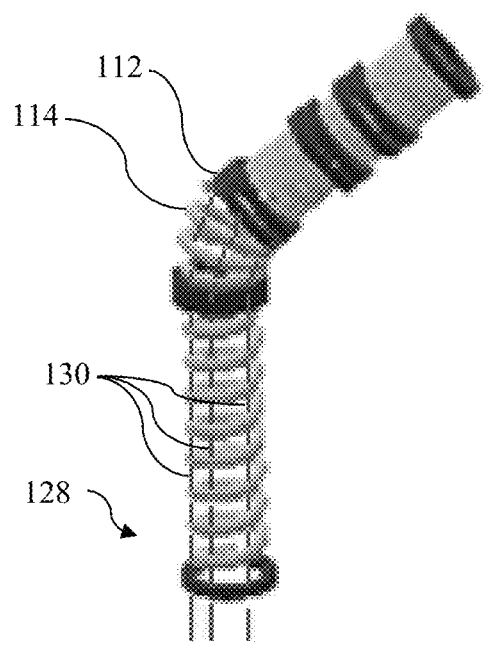
FIG. 4 illustrates the guide tube as in FIG. 1 with a cable assembly according to disclosed embodiments.

Referring also to FIG. 4, the elbows 106 can be oriented using a cable steer system 128 so as to adjust the angle of orientation between the two adjacent connecting structures' respective central axes. For example, for each elbow, four cables 130 (three shown as dotted lines) can extend through the spring 114 and attach at the elbow's distal ring 112 at equal spacing around the ring's circumference. The cables 130 can each be independently protracted and retracted in order to bend the joint's spring so that the spring's distal end extends in a desired direction. Similarly, by protracting (i.e., letting out) cables attached at a distal ring 112 of each linearly elongatable structure 108, the linearly elongatable structures can be selectively elongated along their respective central axes 110 from the compressed state 120 to a selected elongated (decompressed) state 122. Accordingly, because the guide tube as in FIG. 1 has three linearly elongatable structures 108 and two elbows 106, each having four cables in their respective structure, a total of twenty cables extend through the first, most proximal spring, sixteen cables extend through the second spring, etc. In further embodiments, each cable assembly can include more or fewer than four cables. For example, some embodiments can include one, two, three, five, six, or more cables per connecting structure. In some embodiments, the elbows can be bent so that a first axis perpendicular to an opening at a first end can be oriented in 360 degrees about a second axis that extends perpendicularly to the opening at a second end.

In this way, by beginning at a proximal end 124 of the electrode assembly 100 and alternating between expanding the linearly elongatable structures 108 and bending the elbows 106, the guide tube 102 of the electrode assembly 100 can be positioned along a desired path. In this way, an electrode subassembly, disclosed herein, that is positioned within the guide tube, can be positioned so as to allow for multifocal target simulation and recording at various locations along the guide tube's length (for example, as shown in FIG. 2). Similarly, as shown in FIG. 3, the guide tube's path can allow for optimal stimulation of a white matter tract. Moreover, the desired path can be one that minimizes damage to the brain tissue and more precise and efficient enables charge delivery with respect to multifocal targets and white matter tract three dimensional geometry.

While embodiments shown include alternating linearly elongatable structures 108 and angularly orienting elbows 106, it should be understood that in further embodiments, the linearly elongatable structures and angularly orienting joints need not alternate. Moreover, in some embodiments, the connecting structures can comprise a single structure. That is, each can include opposing rings 112, a connecting spring 114, and a plurality of cables 130 that actuate the structure. For example, some embodiments of such a connecting structure can include a four cables extending through the spring 112 and attached at points evenly spaced about the circumference of the distal ring 114. Protracting all four cables by an equal length can allow the spring to extend longitudinally, while protracting two adjacent cables can cause the spring to bend like an elbow, as discussed herein. It is further contemplated that the elbows can have shorter springs 112 than the springs 112 of the linearly elongatable structures. The shorter springs can enable short, tight bends, which can, in some circumstances, avoid tissue damage that might otherwise result from longer, sweeping bends. It is still further contemplated that connecting structures that are configured as linearly elongatable structures can, in some circumstances, be elongated along a curved pathway. For example, one or more of the cables of the connecting structures can be protracted by lengths that are greater than the protraction lengths of the remainder of its cables.

Referring also to FIGS. 5-12, an electrode subassembly 150 having a central axis 152 can extend through the guide tube. In some embodiments, the guide tube can be positioned within the brain, and the electrode subassembly can thereafter be inserted into the guide tube. In further embodiments, the electrode subassembly 150 attaches at a distal end 126 of the electrode assembly 100 so that, as the guide tube is positioned, the electrode subassembly is correspondingly positioned. As discussed below, the electrode subassembly 150 can comprise a plurality of electrodes along its length. Accordingly, a single guide tube can position a plurality of electrodes at a plurality of multifocal targets 159 along the guide tube's length 104. The electrode subassembly 150 can comprise electrode contacts 154 that can each be selectively configured for radial movement about and between a retracted position 156 and a deployed position 158. In the deployed position, the electrode contacts 154 can be spaced radially outwardly from the electrode contacts' respective retracted positions 156. In some embodiments, the electrode contacts can be repeatedly moved between the deployed and the retracted positions.

Figure 5:
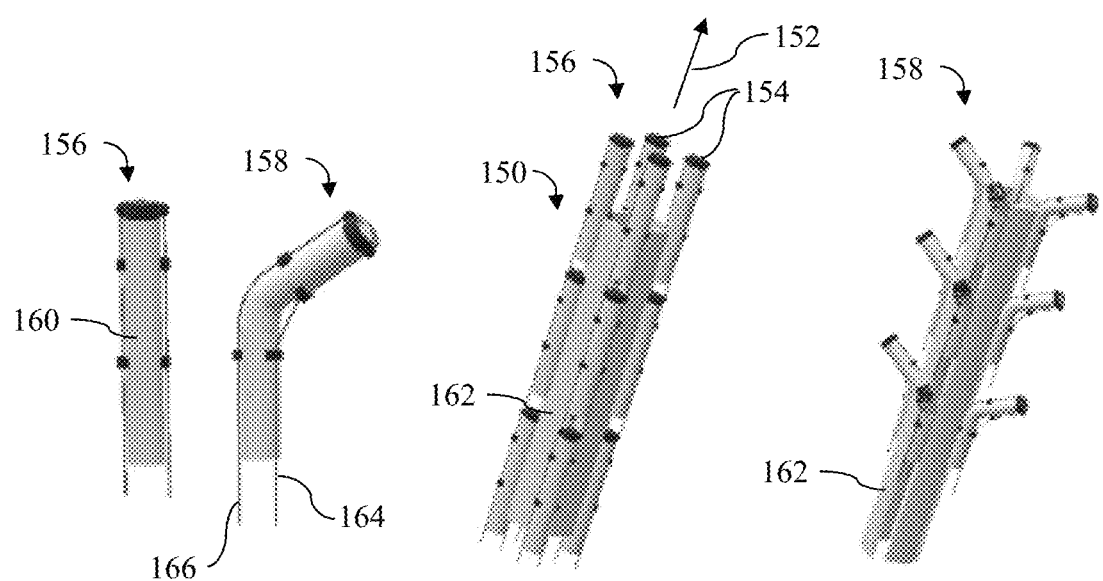
FIG. 5 illustrates a first embodiment of an electrode subassembly for use with the electrode assembly according to disclosed embodiments.
Figure 6A:
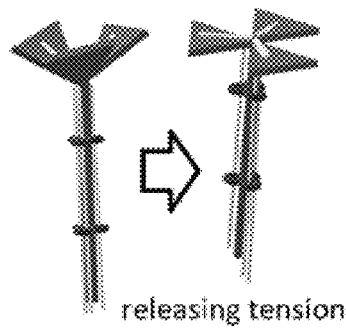
FIGS. 6A-6G illustrate a plurality of perspective views of a second set of embodiments of an electrode subassembly for use with the electrode assembly according to disclosed embodiments.
Figure 6B:
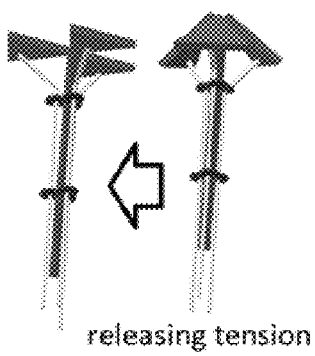
Figures 6C, 6D, 6E:
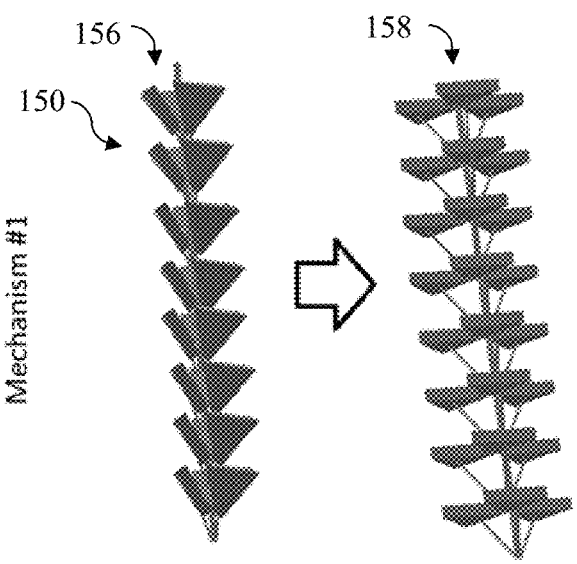

Referring to FIG. 5, the electrode contacts 154 can be disposed at ends of flexible structures (i.e. branches 160) that attach to a frame 162. Cables 164 and 166 can be pulled to actuate respective flexible branches 160. For example, tension on the cable 164 can cause its respective flexible branch 160 to bend so that the respective electrode is positioned outwardly from the electrode subassembly's axis 152 in a deployed position 158. A relaxed amount of tension on the cable 164 and a tension on the cable 166 can cause the respective flexible branch 160 to straighten, thereby positioning the respective electrode is positioned closer to the axis 152 in a retracted position, Flexible structures are shown with cylindrical profiles, but it should be understood that other profiles, e.g., square, can be implemented. Similarly, although the electrodes are shown as circular contacts, the electrodes can take a variety of shapes. For example, FIGS. 6A-C illustrates electrodes 150 having a triangular profile. In a further embodiment, a tension on the cable 164 can cause the respective flexible branch 160 to bend so that the respective electrode is positioned outwardly from the electrode subassembly's axis 152 in a deployed position 158. A relaxed amount of tension on cable 164 can allow the respective flexible branch 160 to straighten under its inherent bias to its respective retracted position closer to the axis 152.

Figure 6F:
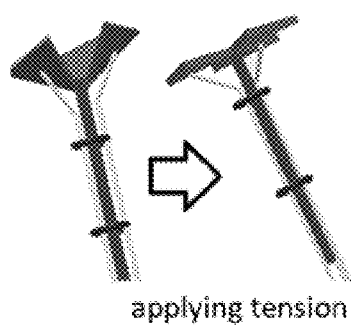
Figure 6G:
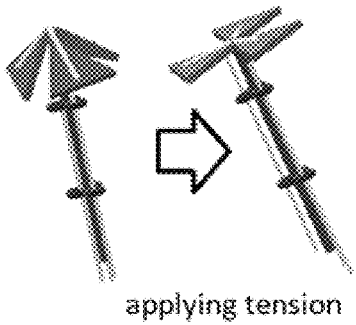

Referring to FIGS. 6A-6G, the electrode contacts 154 can be pivotably attached at a frame 170, and a cable 172 can attach distally of each electrode's pivot axis. The electrode contacts can be biased to a deployed position, such as, for example, extending in a distal direction with respect to the electrode subassembly's axis 152, as in FIGS. 6A and 6C, or extending in a proximal direction, as in 6B and 6E. In this way, tension on the cables can hold their respective electrodes in retracted positions. A release of said tension can cause the electrodes to pivot about their respective attachment hinges to the frame 170, thereby extending the electrode contacts' distal ends outwardly from the electrode subassembly's axis 152 in the deployed position 158. Cables can attach at a distal side (with respect to the electrode subassembly's axis 152) of each respective electrode 150. FIGS. 6A and 6C illustrate cables that attach at a top of the respective electrode so that tension causes the electrodes to retract toward the distal end of the electrode subassembly (upward in the Figures) and release of tension on the cables allows the respective electrodes to pivot under their inherent bias to their respective deployed positions 158. FIGS. 6B and 6E illustrate cables that attach at a bottom of the respective electrode so that tension causes the electrodes to retract toward the proximal end of the electrode subassembly (downward in the Figures) and release of tension on the cables allows the respective electrodes to pivot under their inherent bias to their respective deployed positions 158. In further embodiments, the electrodes can be biased to their retracted position as in FIGS. 6F and 6G, and the cables can be tensioned (i.e., retracted) in order to move the electrodes to their respective deployed positions. When the cable tension is released, the electrodes can move to their retracted position. For example, FIG. 6F illustrates cables that attach at a bottom of the respective electrodes so that tension causes the electrodes to deploy toward the proximal end of the electrode subassembly (downward in the Figures); FIG. 6G illustrates cables that attach at a top of the respective electrodes so that retraction of the cables pulls the electrodes distally (upward in the Figures) to the deployed position.

Figure 7:
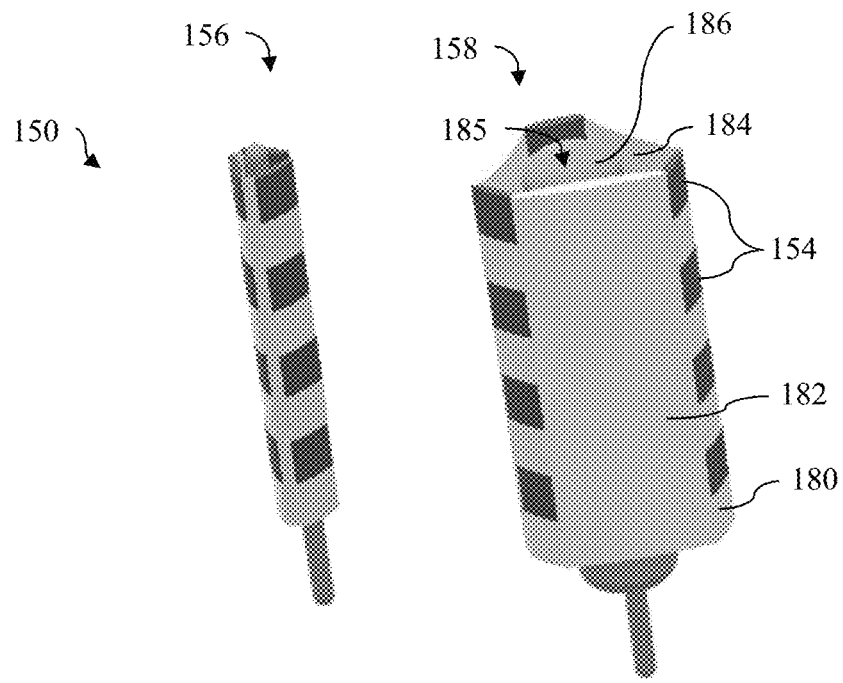
FIG. 7 illustrates a perspective view of a third embodiment of an electrode subassembly for use with the electrode assembly according to disclosed embodiments.

Referring to FIG. 7, the electrode subassembly 150 can include an annular body 180 having an outer surface 182 and an inner surface 184 that defines an axial bore 186. The electrode contacts 154 can attach to the outer surface 182 of the annular body 180. A selectively inflatable balloon 186 can be positioned within the axial bore 185 of the annular body 180. The annular body 180 can comprise a flexible material that permits radial expansion and compression of the annular body in response to selective inflation and deflation of the balloon. The balloon can be attached to the annular body 180 so that retraction of the balloon can cause respective retraction of the annular body.

Figure 8:
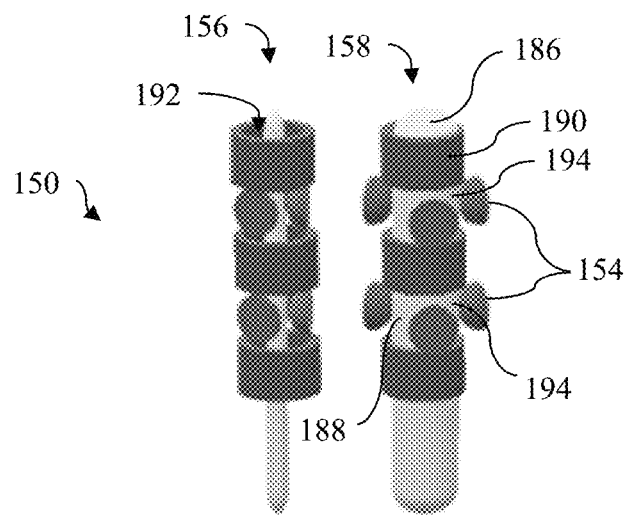
FIG. 8 illustrates a perspective view of a fourth embodiment of an electrode subassembly for use with the electrode assembly according to disclosed embodiments.

Referring to FIG. 8, according to one optional aspect, the electrode assembly can comprise an annular body 190 that defines an axial bore 192 and a plurality of openings 194 that are axially spaced along the annular body's length. A selectively inflatable balloon 186 can be positioned within the axial bore of the annular body. The selectively inflatable balloon 186 can have an outer surface 188, and plurality of electrode contacts 154 can couple thereto. In response to selective inflation and deflation of the balloon 186, the plurality of electrode contacts 154 can be radially expanded and retracted through corresponding openings 194 of the annular body 190.

Figure 9:
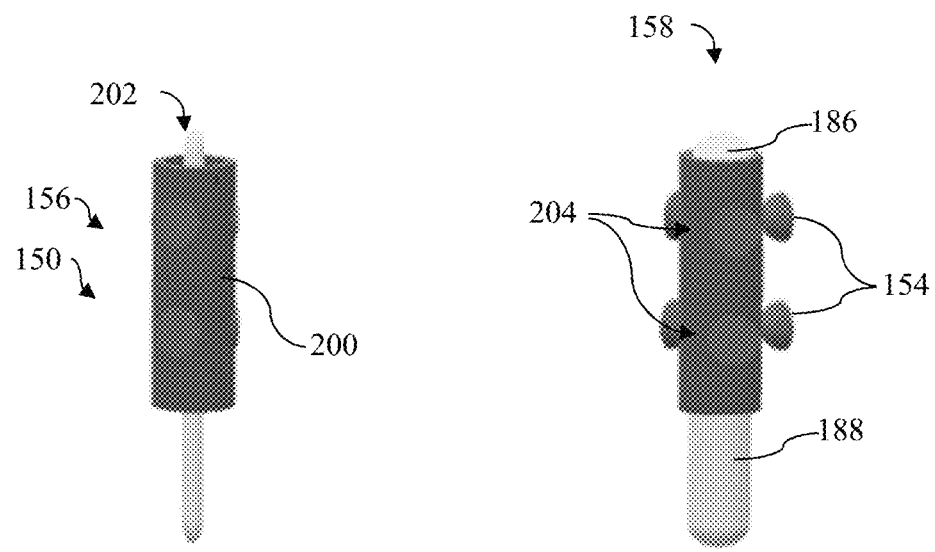
FIG. 9 illustrates a perspective view of a fifth embodiment of an electrode subassembly for use with the electrode assembly according to disclosed embodiments.

Referring to FIG. 9, according to one optional aspect, the electrode assembly can comprise an annular body 200 that defines an axial bore 202 and a plurality of sets of circumferentially spaced openings 204 spaced along the annular body's length. A selectively inflatable balloon 186 can be positioned within the axial bore of the annular body. The selectively inflatable balloon 186 can have an outer surface 188, and plurality of electrode contacts 154 can couple thereto. In response to selective inflation and deflation of the balloon 186, the plurality of electrode contacts 154 can be radially expanded and retracted through corresponding openings 204 of the annular body 200.

Figure 10:
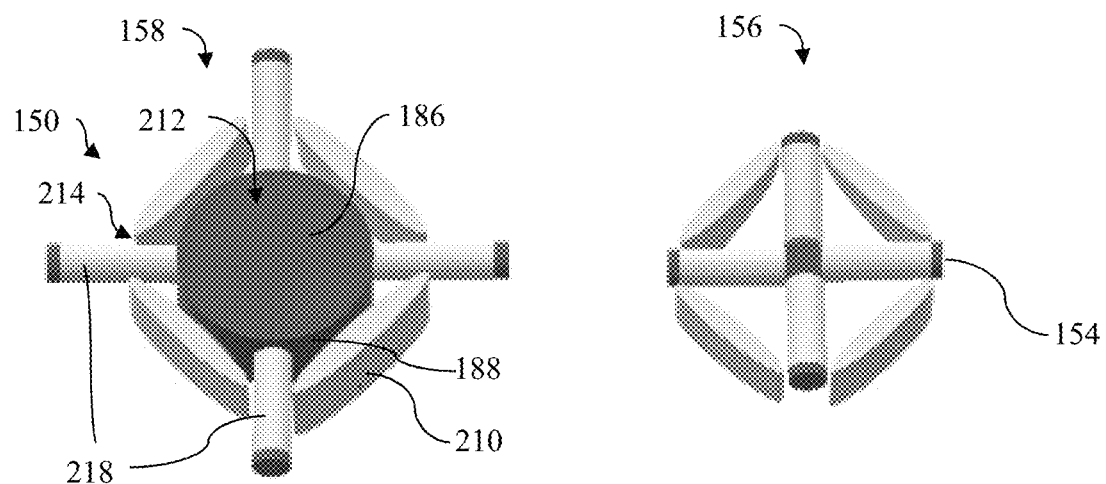
FIG. 10 illustrates a perspective view of a section of a sixth embodiment of an electrode subassembly for use with the electrode assembly according to disclosed embodiments.
Figure 11:
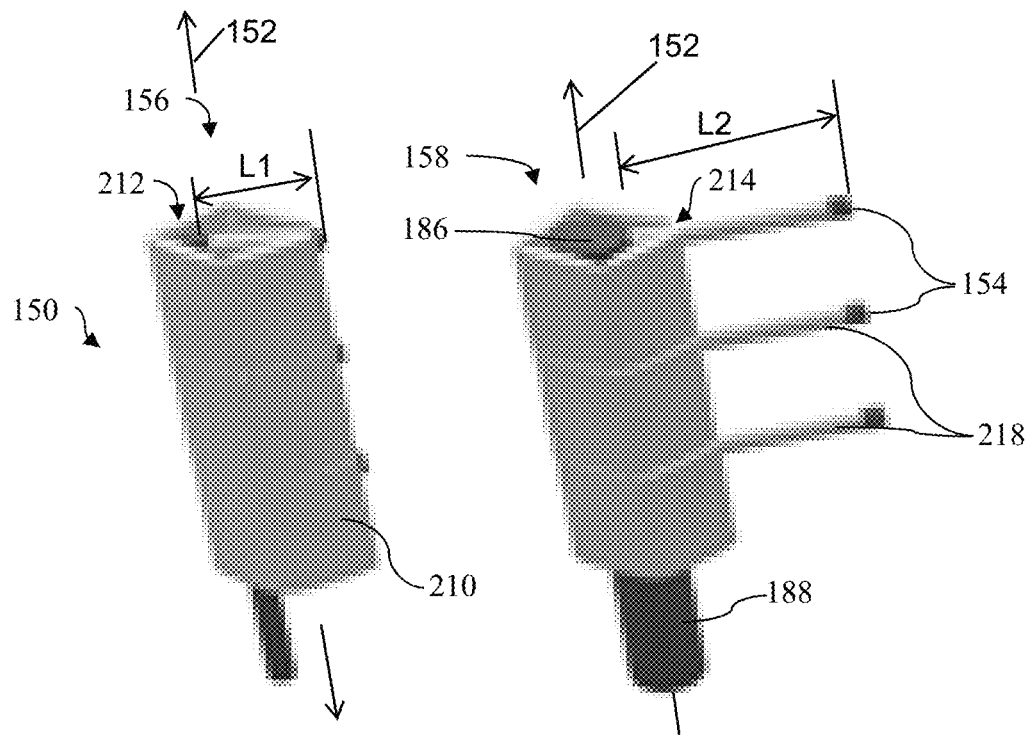
FIG. 11 illustrates a perspective view of a seventh embodiment of an electrode subassembly for use with the electrode assembly according to disclosed embodiments.
Figure 12:
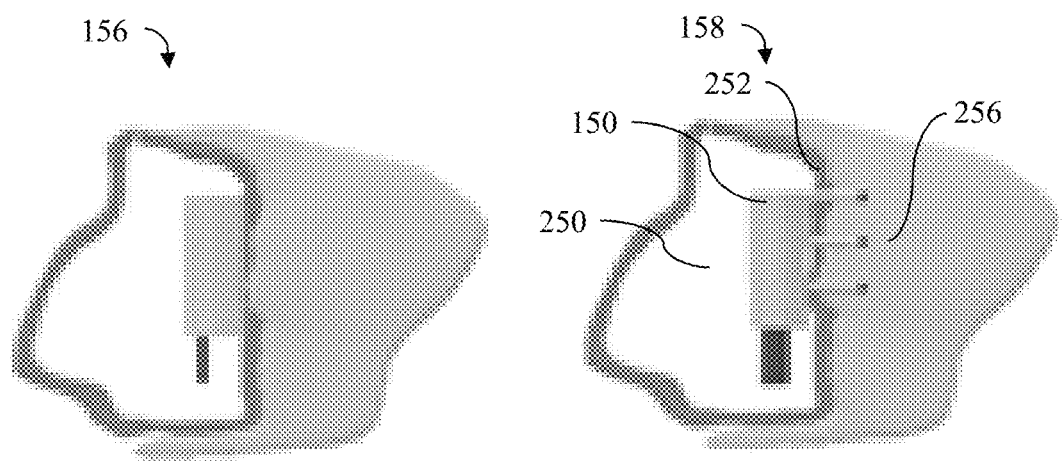
FIG. 12 illustrates a side view of the seventh embodiment of an electrode subassembly positioned within a tissue.
Figure 13:
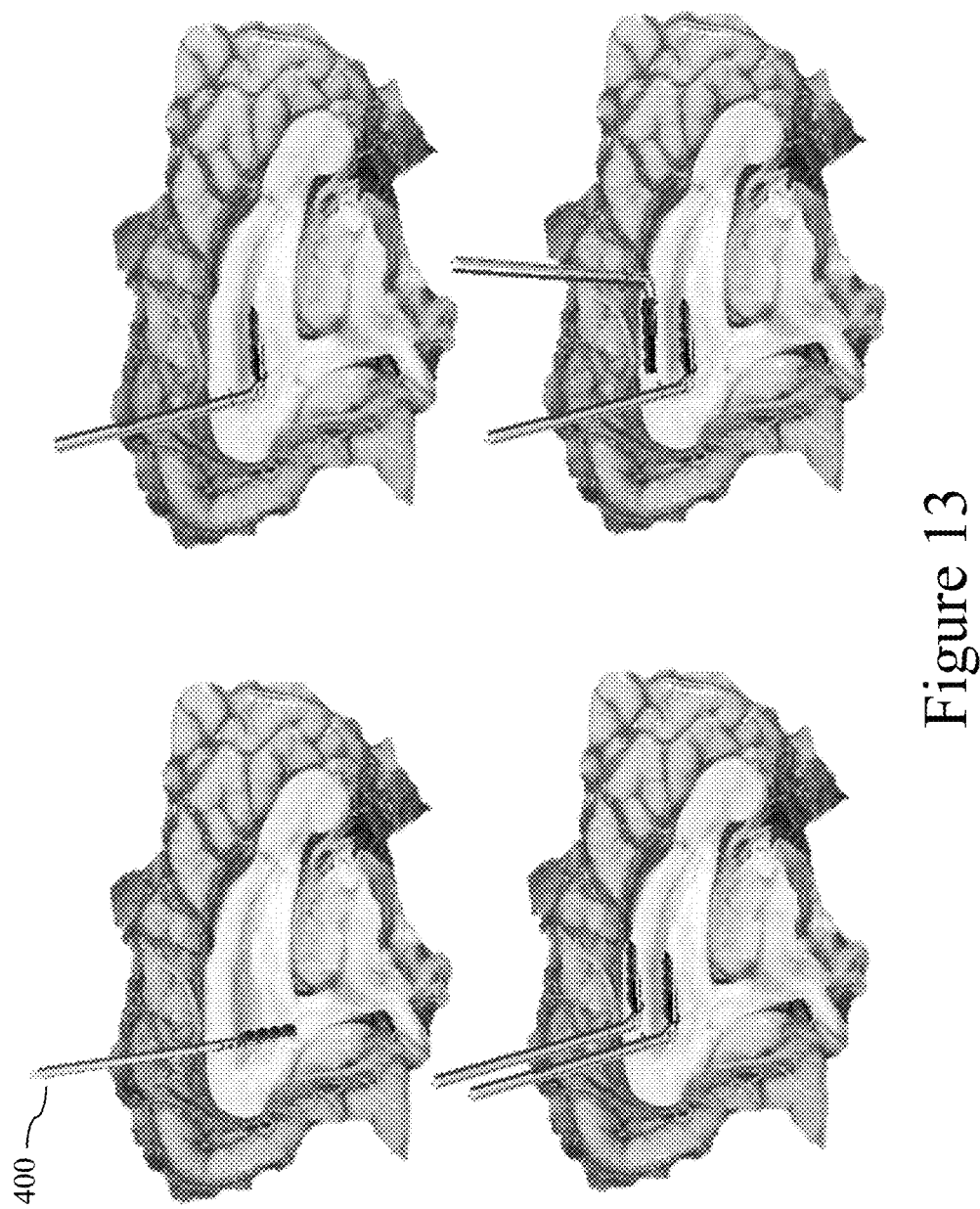
FIG. 13 illustrates various positions of corpus callosum stimulating electrode assemblies disposed within a brain.

Referring to FIG. 10-12, according to one optional aspect, the electrode assembly can comprise an annular body 210 that defines an axial bore 212 and a plurality of openings 214. A selectively inflatable balloon 186 can be positioned within the axial bore of the annular body. The selectively inflatable balloon 186 can have an outer surface 188. A plurality of rods 218 extend radially outwardly from and are coupled to the outer surface of the balloon. A respective electrode contact 154 is secured to a distal end of each rod 218. In response to selective inflation and deflation of the balloon 186, the plurality of rods 218 are configured for radial movement. In some embodiments, the rods can be circumferentially spaced about the outer surface of the balloon, as in FIG. 10. In some embodiments, the rods 218 can be axially spaced along an axial length of the balloon, as in FIGS. 11-12. According to some aspects, circumferentially spaced rods can be positioned at a plurality of intervals along the axial length of the balloon. Accordingly, it can be understood that FIG. 10 illustrates a portion of an electrode assembly showing a first plurality of circumferentially spaced rods, and similar pluralities of circumferentially spaced rods can be positioned along the axial length of the balloon. In some embodiments, the rods 218 can be electrodes, rather than having electrodes attached at distal ends.

Still referring to FIGS. 11-12, at least one rod 218 of the plurality of rods can have a first radial length L1 in a dimension perpendicular to the central axis 152 when the electrode subassembly 150 is in the retracted configuration (FIG. 11, left) and a second radial length L2 in said dimension perpendicular to the central axis 152 that is greater than the first radial length L1 when the electrode subassembly is in the deployed configuration.

Referring to FIGS. 13-17, an electrode assembly 300 for stimulating the corpus callosum and white matter tracts is shown.

Figure 14:
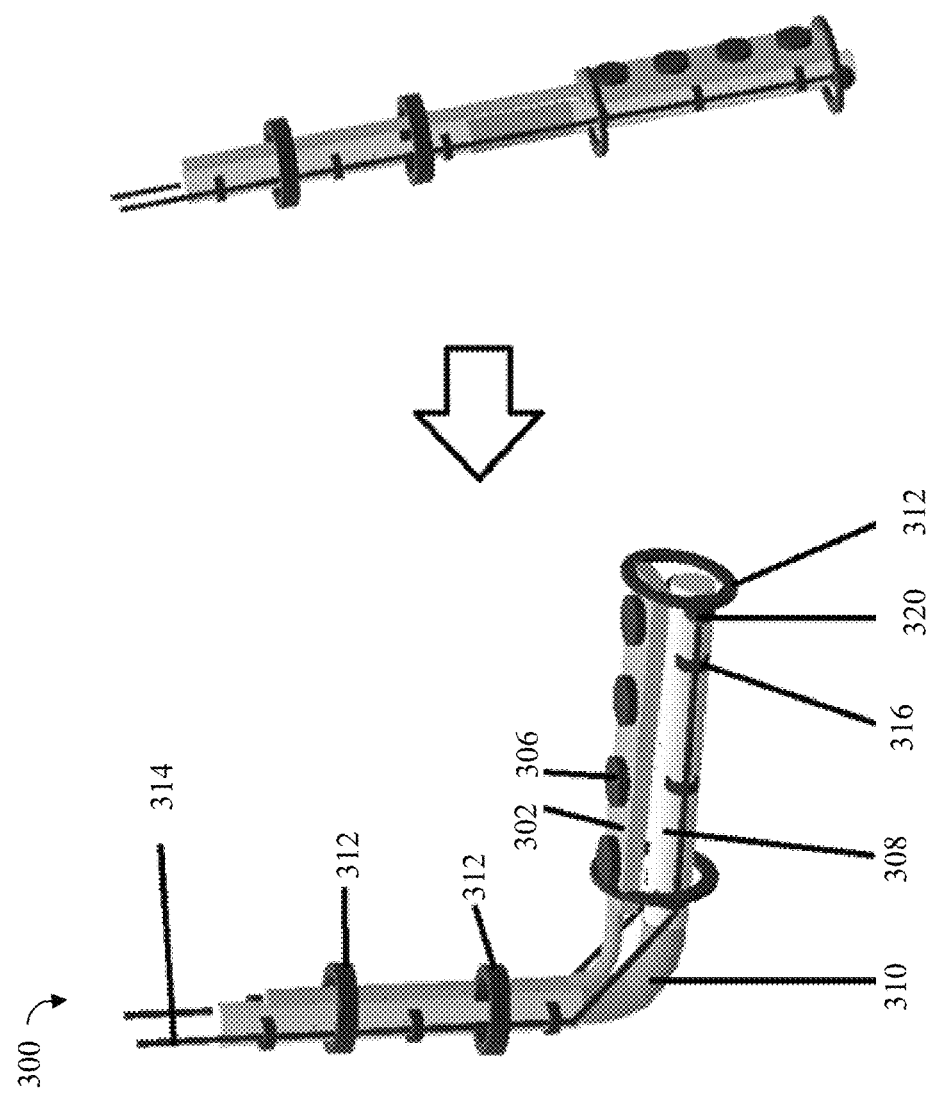
FIG. 14 illustrates a first embodiment of a corpus callosum stimulating electrode assembly according to disclosed embodiments.

Referring to FIG. 14, the electrode assembly 300 can include a cortical strip lead 302 including electrical contacts 306. A pair of rigid rods 308 couple via a flexible joint 310 to provide a structural member. Rings 312 can couple the strip lead 302 to the structural member. Actuation cables 314 can slidably engage the structural member via loops 316. Distal ends of the cables can attach to a distal rings 312 at respective connection points 320. Accordingly, the electrode assembly 300 can be inserted into the brain and actuated via tension on the cables to position the cortical strip lead 102 in a desired location. In a further embodiment, a depth electrode can be used instead of cortical strip lead.

Figure 15:
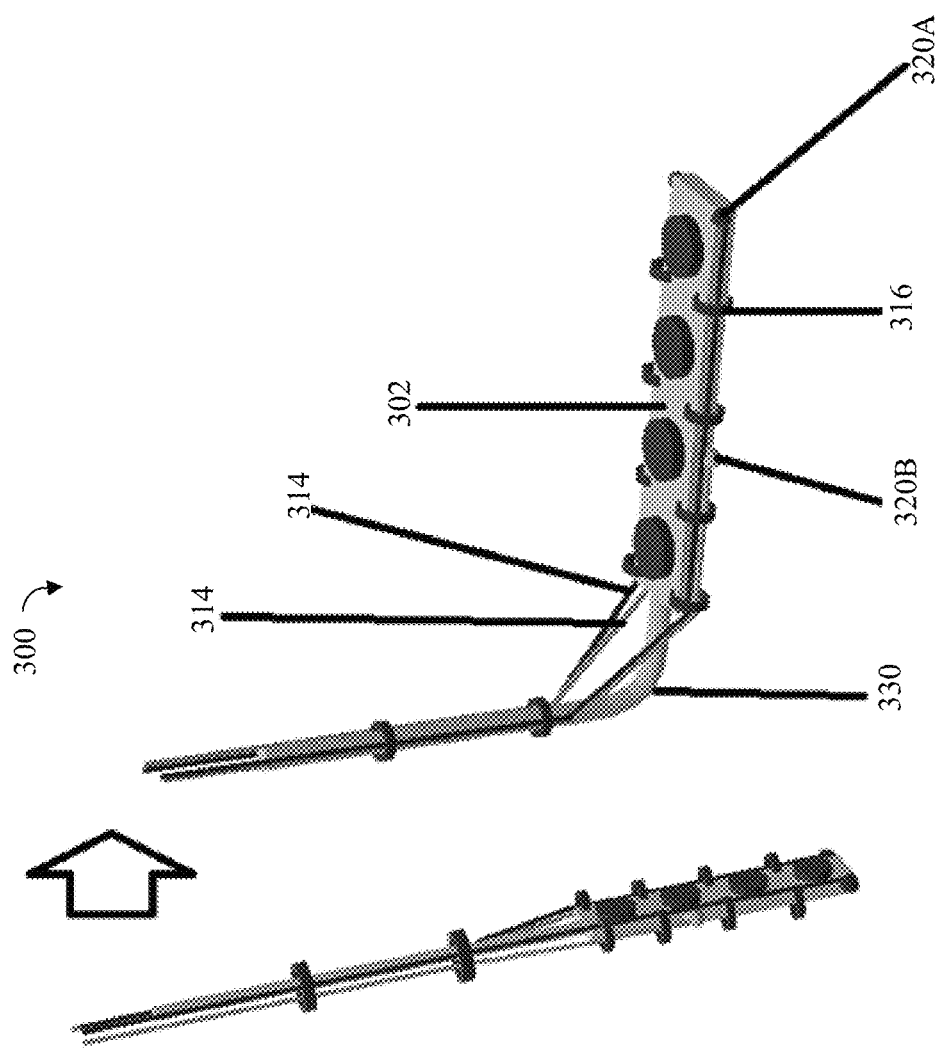
FIG. 15 illustrates a second embodiment of a corpus callosum stimulating electrode assembly according to disclosed embodiments.

Referring to FIG. 15, another embodiment, of an electrode assembly 300 can include a strip lead 302. The strip lead can include a rigid portion and a flexible joint 330. Loops 316 can attach to the strip lead 302 and receive cables 314 therethrough. A first pair of cables can attach at respective attachment points 320A at a distal end of the strip lead 302, and a second pair of cables can attach at attachment points 320B spaced away from the distal end of the strip lead. Tension on the cables can cause the electrode assembly to bend to a flexed position.

Figure 16:
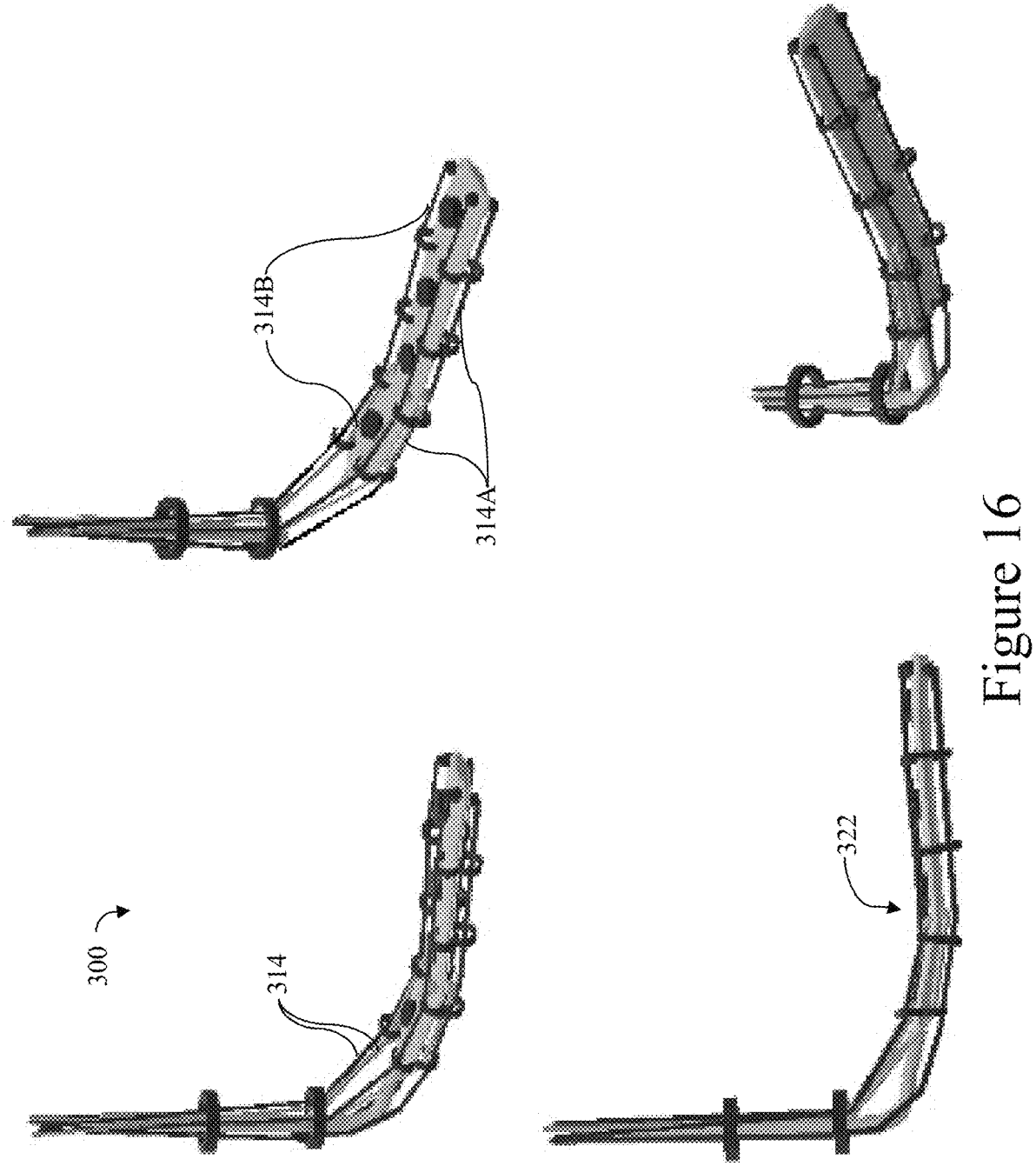
FIG. 16 illustrates a third embodiment of a corpus callosum stimulating electrode assembly according to disclosed embodiments.

Referring to FIG. 16, a similar embodiment as to that of FIG. 15 is shown, except that the cables 314 can attach at top and bottom sides of the lead strip. Accordingly, tension on cables 314B at the top can cause the electrode assembly 300 to move to a flexed position, and tension on cables 314A at a bottom of the lead strip can cause the electrode assembly to return to the straight position. Moreover one or more (e.g., two shown) cables 314B can attach at a distal end of the lead strip, and one or more (e.g., two shown) cables 314B can attach at a proximal end of the lead strip. Similarly, one or more (e.g., two shown) cables 314A can attach at a distal end of the lead strip, and one or more (e.g., two shown) cables 314A can attach at a proximal end of the lead strip. In this way, tension on each of the distally attaching and proximally attaching can be selected in order to provide a select shape/curvature of the lead strip. For example, a bend 322 can be formed in the lead strip, thereby positioning its electrodes on a desired curve in 3D space. Varying numbers of cables and attachment points along the lead strip's length can enable various amounts of articulation in the lead strip.

Figure 17:
FIG. 17 illustrates a corpus callosum stimulating electrode assembly curved around white matter of a brain.

Referring to FIG. 17, the electrode assembly 300 can have a curved profile when flexed. In this way, the electrode assembly can encompass target white matter tracts more efficiently, and, consequently, with more efficient stimulation, than straight configurations.

Using the electrode assembly as discussed herein, the electrode subassembly can be positioned at a selected position within a selected tissue region. When the electrode subassembly is positioned, at least a first portion of a plurality of electrode contacts of the electrode subassembly can be moved from the retracted position to the deployed position. The at least a first portion of the plurality of electrode contacts can then be retracted from the deployed position. A second portion of the plurality of electrode contacts of the plurality of electrode contacts can be moved from the retracted position to the deployed position. For example, with reference to the cable-actuated embodiments shown in FIGS. 5 and 6, separate cables can attach to separate electrodes or groups of electrodes. Accordingly, each cable can independently actuate its respective electrode(s). With reference to the embodiments shown with inflatable balloons, each subassembly can include a plurality of balloons that can each be independently inflated and deflated.

Referring to FIG. 12, the electrode subassembly can be positioned at tissue region, such as, for example at a ventricle 250. Once the electrode subassembly is positioned, the electrode contacts can be moved to a deployed position at a tissue region. For example, in response to selective inflation of the balloon, the plurality of rods can undergo corresponding radial movement into a target tissue 256. The target tissue can include, for example, brain parenchyma. The electrode contacts can enter the target tissue through a wall 252 of the ventricle 250. Once the electrode contacts have been moved to a deployed position at a tissue region, the electrode contacts can be activated to stimulate tissue at the tissue region. The electrodes can further be used to record brain activity.

In several neurological conditions (e.g. large cortical dysplasia), the pathologic tissue is significantly larger than the spatial effective distribution of the electric field of the relatively smaller stimulation electrodes. Thus, neuromodulation of large cortical pathologic tissue will be suboptimal. Stimulation of small cross-sectional diameter of compact white matter axons allows the electric current to propagate to the large cortical pathologic tissue and modulates its function more efficiency in comparison to direct stimulation of cortical tissue. Stimulation of many central nervous systems structures, in various forms, has been proposed. However, conventionally, white matter tracts within corona radiate region have not been examined. In order to stimulate a specific part of white matter tract in a three-dimensional arrangement using conventional electrodes and conventional implantation methods currently used in clinical practice, it is necessary to implant multiple electrodes through multiple trajectories with different orientations, which might result in a significant tissue damage along the trajectories and because of suboptimal three dimensional arrangement of stimulation electrode contacts with respect to the target white matter tract, spatial electric field might not be optimal to modulate the target white matter tracts. In contrast with conventional electrodes currently used in clinical practice, using the disclosed guide tube and stimulation electrode assembly, electrodes can be flexibly implanted in a three dimensional curved trajectory to provides optimal stimulation. In addition, in order to refine the neurostimulation efficacy, using proposed retractable and deployable mechanism, spatial location of the electrode contacts can be rearranged anytime during the chronic implantation period.

The electrode subassemblies 150, as illustrated in FIGS. 5-12, can, in their respective retracted positions, have a diameter that is significantly smaller than the guide tube diameter. Moreover, each of flexible structures 160, frames 162, 170, and annular bodies 180, 190, 200, 210 can be flexible. In this way, the electrode subassemblies can be advanced in their respective guide tubes, even at the elbows where the guide tubes change directions. (It should be understood that, in their deployed positions, the electrodes can extend beyond the diameter of the guide tube, thereby engaging the tissue.)

Figure 18:
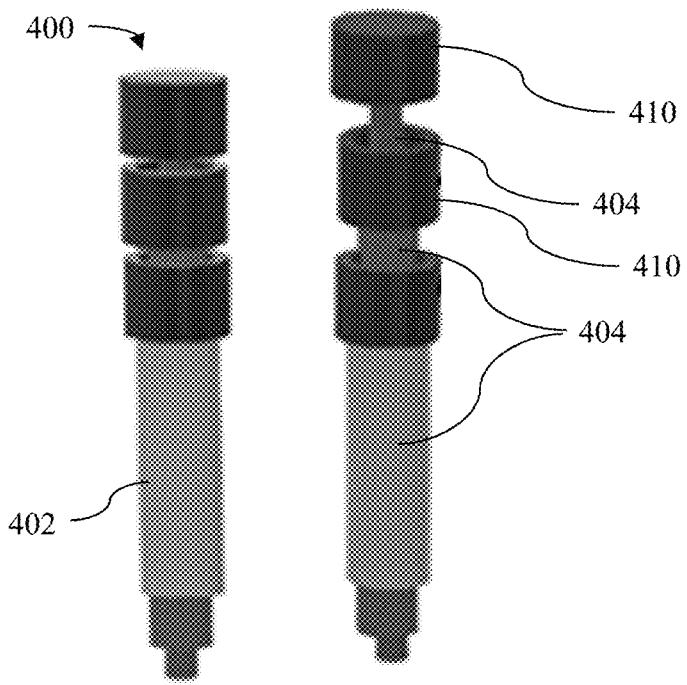
FIG. 18 illustrates a first axially extending electrode subassembly.
Figure 19:
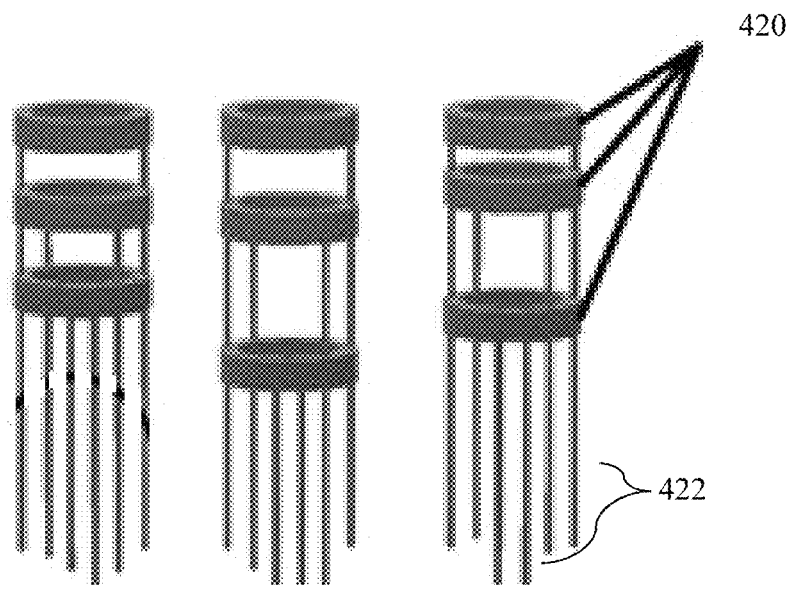
FIG. 19 illustrates a second axially extending electrode subassembly.
Figure 20:
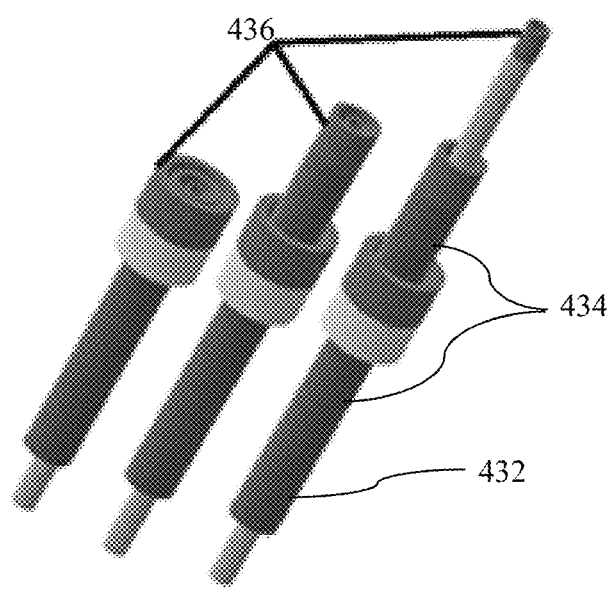
FIG. 20 illustrates a third axially extending electrode subassembly.

Referring to FIGS. 18-20, axially extendable electrode assemblies are disclosed. The axially extendable electrode assemblies can be inserted into guide tubes 102 in order to position electrodes. FIG. 18 illustrates a recording and stimulation electrode assembly 400 having a telescoping structure 402 that includes a plurality of nesting hollow cylinders 404 that can slide within respective adjacent larger cylinders. Electrodes 410 can attach at distal ends of respective hollow cylinders 404.

Referring to FIG. 19, annular electrodes 420 can be supported by a frame (not shown) and respective pairs of actuation cables 422 can attach to each annular electrode 420. The actuation cables can be used for positioning each contact as well as acting as a conductor for each contact. In some embodiments, the actuation cables 422 can extend through small holes in rings of more proximal electrodes 420. In further embodiments, the actuation cables 422 can extend through the interior of the proximal electrode annuluses.

Referring to FIG. 20, a telescoping structure 432 can include nesting hollow cylinders 434. Annular electrode contacts 436 at distal ends of respective hollow cylinders 434 can similarly nest within each other. Each electrode subassembly (e.g., the hollow cylinder 434 and respective electrode contact 436 of FIG. 20 and annular electrode 420 and respective actuation cables 422 of FIG. 19) can be independently repositioned from the axially extendable electrode assembly's proximal end.

In some embodiments, aspects of the axially extending electrode assemblies can be incorporated with the deployable electrode subassemblies as disclosed herein. For example, materials for structures 402, 432 can be selected from flexible materials. Accordingly, the electrode subassemblies can be both moved between deployed and retracted positions as well as repositioned along the length of the guide tube.

In still further aspects, the guide tube can comprise stimulating/recording contacts. For example, referring to FIG. 1, the rings 112 can be electrodes that can be configured to stimulate tissue and/or record signals (e.g., brain activity) from the tissue. In further aspects, the springs 114 or the entire connecting structure 110 can each be a stimulating/recording electrode. In further aspects, electrodes can be attached to the guide tube along the length of the guide tube (e.g., in spaced relation along the length of the guide tube). For example, electrodes can attach to one or more of the rings 112 of the guide tube 102. Accordingly, it is contemplated that the guide tube itself can be used as a recording and stimulating module. Thus, according to some optional embodiments, a separate electrode assembly can be excluded.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A neural stimulation and recording electrode assembly comprising: a selectively deformable guide tube having a length and including: a plurality of sequentially coupled connecting structures, wherein each connecting structure of the plurality of connecting structures has a respective central axis, and wherein at least one of the plurality of connecting structures is selectively deformable relative to the central axis of a sequential connecting structure of the plurality of connecting structures such that the central axis of the selectively deformable connecting structure is angularly oriented relative to the central axis of the sequential connecting structure; and an electrode subassembly having a central axis and a plurality of electrode contacts that are configured for selective radial movement about and between a retracted position and a deployed position, wherein in the deployed position, and relative to the central axis, each electrode contact is spaced radially outwardly from the retracted position.

Aspect 2: The neural stimulation and recording electrode assembly of aspect 1, wherein each of the at least one selectively deformable connecting structures of the guide tube is configured to be selectively independently deformed as the selectively deformable connecting structure is advanced within a tissue region.

Aspect 3: The neural stimulation and recording electrode assembly of aspect 1 or aspect 2, wherein each of the plurality of connecting structures is selectively deformable relative to the central axis of a sequential connecting structure of the plurality of connecting structures such that the central axis of the selectively deformable connecting structure is angularly oriented relative to the central axis of the sequential connecting structure.

Aspect 4: The neural stimulation and recording electrode assembly of any one of the preceding aspects, wherein each of the at least one selectively deformable connecting structures is selectively compressible and expandable relative to the central axis of the connecting structure, wherein the selectively deformable guide tube is deformable from a first compressed orientation to a second expanded orientation, and wherein in the second expanded orientation, at least one of the selectively deformable connecting structures is axially expanded in comparison to the first compressed orientation.

Aspect 5: The neural stimulation and recording electrode assembly of any one of the preceding aspects, wherein each of the plurality of connecting structures comprise springs.

Aspect 6: The neural stimulation and recording electrode assembly of aspect 5, wherein each of the connecting structures further comprises rings attached at each end of the spring of the respective connecting structure.

Aspect 7: The neural stimulation and recording electrode assembly of aspect 1, wherein the length of at least one connecting structure of the plurality of connecting structures is different than the length of at least one other connecting structure of the plurality of connecting structures.

Aspect 8: The neural stimulation and recording electrode assembly of any one of the preceding aspects, wherein the plurality of connecting structures comprises at least one joint, and at least one linearly elongatable structure, wherein each joint of the at, least one joints and each linearly elongatable structure of the at least one linearly elongatable structure have respective lengths, and wherein the length of each linearly elongatable structure is greater than the length of each joint.

Aspect 9: The neural stimulation and recording electrode assembly of any one of the preceding aspects, wherein the electrode subassembly comprises a plurality of branches extending radially outwardly from the central axis of the electrode subassembly, wherein the plurality of electrode contacts are provided on respective branches of the plurality of branches, wherein each branch is selectively radially moveable to effect movement of a corresponding electrode contact about and between the retracted position and the deployed position.

Aspect 10: The neural stimulation and recording electrode assembly of aspect 9, wherein each branch is selectively angularly deformable relative to the central axis of the shaft to effect movement of a corresponding electrode contact about and between the retracted position and the deployed position.

Aspect 11: The neural stimulation and recording electrode array of any one of aspects 1-8, wherein the electrode subassembly further comprises: an annular body having an outer surface and an inner surface that defines an axial bore, wherein the plurality of electrode contacts are coupled to the outer surface of the annular body; and a selectively inflatable balloon positioned within the axial bore of the annular body, wherein the annular body comprises a flexible material that permits radial expansion and compression of the annular body in response to selective inflation and deflation of the balloon.

Aspect 12: The neural stimulation and recording electrode array of any one of aspects 1-8, wherein the electrode subassembly further comprises: an annular body defining an axial bore and a plurality of sets of circumferentially spaced openings, wherein the plurality of sets are axially spaced along a length of the annular body; and a selectively inflatable balloon positioned within the axial bore of the annular body, wherein the selectively inflatable balloon has an outer surface to which the plurality of electrode contacts are coupled, wherein, in response to selective inflation and deflation of the balloon, the plurality of electrode contacts are configured for radial expansion and retraction through corresponding openings of the annular body.

Aspect 13: The neural stimulation and recording electrode array of any one of aspects 1-8, wherein the electrode subassembly further comprises: an annular body defining an axial bore and a plurality of openings that are axially spaced along a length of the annular body; and a selectively inflatable balloon positioned within the axial bore of the annular body, wherein the selectively inflatable balloon has an outer surface to which the plurality of electrode contacts are coupled, wherein, in response to selective inflation and deflation of the balloon, the plurality of electrode contacts are configured for radial expansion and retraction through corresponding openings of the annular body.

Aspect 14: The neural stimulation and recording electrode array of any one of aspects 1-8, wherein the electrode subassembly further comprises: an annular body defining an axial bore and a plurality of openings; a selectively inflatable balloon positioned within the axial bore of the annular body, wherein the selectively inflatable balloon has an outer surface; and a plurality of rods extending radially outwardly from and being coupled to the outer surface of the balloon, wherein a respective electrode contact is secured to a distal end of each rod, wherein, in response to selective inflation and deflation of the balloon, the plurality of rods are configured for corresponding radial movement.

Aspect 15: The neural stimulation and recording electrode array of aspect 14, wherein the plurality of rods are circumferentially spaced about the outer surface of the balloon.

Aspect 16: The neural stimulation and recording electrode array of aspect 14, wherein the plurality of rods are axially spaced along an axial length of the balloon.

Aspect 17: A method of using the neural stimulation and recording electrode array of any one of the preceding aspects, comprising: selectively and sequentially deforming at least one connecting structure of the guide tube to define an insertion pathway; and advancing the electrode subassembly through the guide tube until at least a portion of the plurality of electrode contacts are positioned at a selected position within selected a tissue region; effecting movement of at least a first portion of the plurality of electrode contacts from the retracted position to the deployed position.

Aspect 18: The method of aspect 17, further comprising: retracting the at least a first portion of the plurality of electrode contacts from the deployed position to the retracted position; adjusting the position of the electrode subassembly within the tissue region; and effecting movement of a second portion of the plurality of electrode contacts from the retracted position to the deployed position.

Aspect 19: The method of aspect 18, wherein at least one electrode contact of the second portion of the plurality of electrode contacts is not in included in the first portion of the plurality of electrode contacts.

Aspect 20. The method of any one of aspects 17-19, further comprising: electrically stimulating tissue within the tissue region using the plurality of electrode contacts.

Aspect 21: The method of any one of aspects 17-20, wherein the electrode subassembly comprises: an annular body defining an axial bore and a plurality of openings; a selectively inflatable balloon positioned within the axial bore of the annular body, wherein the selectively inflatable balloon has an outer surface; and a plurality of rods extending radially outwardly from and being coupled to the outer surface of the balloon, wherein a respective electrode contact is secured to a distal end of each rod, wherein, in response to selective inflation of the balloon, the plurality of rods undergo corresponding radial movement to enter into target tissue.

Aspect 22: The method of aspect 21, wherein the target tissue comprises brain parenchyma, and wherein the plurality of rods and corresponding electrode contacts enter target tissue through a ventricle wall.

Aspect 23: An assembly having a length and comprising: plurality of sequentially coupled connecting structures, wherein each connecting structure of the plurality of connecting structures has a respective central axis, and wherein at least two of the plurality of connecting structures is selectively deformable relative to the central axis of a sequential connecting structure of the plurality of connecting structures such that the central axis of the selectively deformable connecting structure is angularly oriented relative to the central axis of the sequential connecting structure.

Aspect 24: The assembly of aspect 23, wherein the assembly comprises a plurality of electrodes positioned along the length of the length of the assembly.

Aspect 25: The assembly of aspect 23, wherein at least a portion of at least one connecting structure is configured to provide electrical stimulation to a tissue.

Aspect 26: An electrode subassembly as disclosed herein.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. An electrode subassembly that is configured for stimulating brain matter and receiving signals from the brain matter, the electrode subassembly being configured for movement about and between a deployed configuration and a retracted configuration, the electrode subassembly having a central axis, the electrode subassembly comprising:
   an annular body defining an axial bore and a plurality of openings;
   a selectively inflatable balloon positioned within the axial bore of the annular body, wherein the selectively inflatable balloon has an outer surface;
   a plurality of rods extending radially outwardly from and being coupled to the outer surface of the balloon, each rod of the plurality of rods having a distal end; and
   a plurality of electrode contacts, wherein a respective electrode contact is secured to the distal end of each rod;
   wherein, in response to selective inflation of the balloon, the plurality of rods are configured for corresponding radial movement outwardly from the central axis.

2. The electrode subassembly of claim 1, wherein the plurality of openings are axially spaced along the central axis.

3. The electrode subassembly of claim 2, wherein the plurality of openings are all positioned on a single side of the annular body.

4. The electrode subassembly of claim 1, wherein the plurality of openings comprise at least one set of openings that are circumferentially spaced about the central axis.

5. The electrode subassembly of claim 4, wherein the at least one set of openings that are that are circumferentially spaced about the central axis comprises a plurality of sets of openings, wherein the plurality of sets of openings are axially spaced along the central axis of the electrode subassembly.

6. The electrode subassembly of claim 1, wherein the annular body has a generally cylindrical outer surface.

7. The electrode subassembly of claim 1, wherein the plurality of rods are rigid rods.

8. The electrode subassembly of claim 1, wherein at least one rod of the plurality of rods has a first radial length in a dimension perpendicular to the central axis when the electrode subassembly is in the retracted configuration and a second radial length that is greater than the first radial length in the dimension that is perpendicular to the central axis when the electrode subassembly is in the deployed configuration.

9. A method comprising:
  positioning an electrode subassembly proximate to a target tissue, wherein the electrode subassembly has a central axis, wherein the electrode subassembly comprises:
    an annular body defining an axial bore and a plurality of openings;
    a selectively inflatable balloon positioned within the axial bore of the annular body, wherein the selectively inflatable balloon has an outer surface; and
    a plurality of rods extending radially outwardly from and being coupled to the outer surface of the balloon, each rod of the plurality of rods having a distal end,
    a plurality of electrode contacts, wherein a respective electrode contact is secured to the distal end of each rod;
  inflating the balloon of the electrode subassembly to move the plurality of electrode contacts radially outwardly toward the target tissue.

10. The method of claim 9, further comprising: stimulating, by at least one electrode contact of the plurality of electrode contacts, the target tissue.

11. The method of claim 9, further comprising receiving, by at least one electrode contact of the plurality of electrode contacts, signals indicative of brain activity.

12. The method of claim 9, wherein positioning the electrode subassembly proximate to the target tissue comprises positioning the electrode subassembly in a ventricle proximate to the target tissue.

13. The method of claim 12, wherein inflating the balloon of the electrode subassembly to move the plurality of electrode contacts radially outwardly toward the target tissue moves the electrodes through a wall of the ventricle.

14. The method of claim 9, wherein the plurality of openings are axially spaced along the central axis.

15. The method of claim 14, wherein the plurality of openings are all positioned on a single side of the annular body.

16. The method of claim 9, wherein the plurality of openings comprise at least one set of openings that are circumferentially spaced about the central axis.

17. The method of claim 9, wherein the at least one set of openings that are that are circumferentially spaced about the central axis comprises a plurality of sets of openings, wherein the plurality of sets of openings are axially spaced along the central axis of the electrode subassembly.

18. The method of claim 9, wherein the annular body has a generally cylindrical outer surface.

19. The method of claim 9, wherein the plurality of rods are rigid rods.

20. The method of claim 9, wherein at least one rod of the plurality of rods has a first radial length in a dimension perpendicular to the central axis when the electrode subassembly is in the retracted configuration and a second radial length that is greater than the first radial length in the dimension that is perpendicular to the central axis when the electrode subassembly is in the deployed configuration.

* * * * *